United States Patent [19]
Horoszewicz

[11] Patent Number: 5,763,202
[45] Date of Patent: Jun. 9, 1998

[54] METHODS OF DETECTING PROSTATE CARCINOMA USING A MONOCLONAL ANTIBODY TO A NEW ANTIGENIC MARKER IN EPITHELIAL PROSTATIC CELLS ALONE OR WITH A MONOCLONAL ANTIBODY TO AN ANTIGEN OF LNCAP CELLS

[75] Inventor: Julius S. Horoszewicz, Williamsville, N.Y.

[73] Assignee: Cytogen Corporation, Princeton, N.J.

[21] Appl. No.: 482,515

[22] Filed: Jun. 7, 1995

Related U.S. Application Data

[63] Continuation of Ser. No. 307,544, Sep. 16, 1994, Pat. No. 5,578,484, which is a continuation of Ser. No. 822,500, Jan. 17, 1992, abandoned, which is a division of Ser. No. 202,869, Jun. 3, 1988, Pat. No. 5,162,504.

[51] Int. Cl.$^6$ .......................... G01N 33/574; C12P 21/04; C12N 15/00; C07K 16/00
[52] U.S. Cl. .................. 435/7.23; 435/70.21; 435/172.2; 435/344; 530/388.8
[58] Field of Search ................... 530/388.8; 435/240.27, 435/7.23, 70.21, 172.2, 344

[56] References Cited

U.S. PATENT DOCUMENTS 4,536,479  8/1985  Vander-Mallie ........................ 436/537

OTHER PUBLICATIONS

Casali et al., Science 234:476–479, 1986.
Sevier et al., Clin. Chem. 27(11):1797–1886, 1981.
Frankel et al., Cancer Res. 42:3714–3718, 1982.
Ware et al., Cancer Res. 42:1215–1222, 1982.
Wisdom, Clinical Chemistry 22:1243–1255, 1976.
ATCC Catalog of Cell lines and Hybridomas, 1988, p. 170.
Horoszewicz et al., 14th International Cancer Congress Abstracts of Lectures, Symposia, Free Communication vol. 1, 1986, p. 150.
Frankel et al., Proc. Nat'l. Acad. Sci. USA 79:903–907, 1982.
Webb et al., Cancer Immunol. Immunother. 17:7–17, 1984.
Finstad et al., Proc. Nat'l. Acad Sci. USA 82:P2955–2959, 1985.
Campbell, "Monoclonal Antibody Technology" Elsevier Publ. 1984.
Wright et al., Cancer Res. 43:5509–5516, 1983.
Horoszewicz et al., Anticancer Res. 7:927–936, 1987.

*Primary Examiner*—Paula K. Hutzell
*Assistant Examiner*—Mark Navarro
*Attorney, Agent, or Firm*—Pennie & Edmonds

[57] ABSTRACT

Monoclonal antibodies to prostatic cells, are produced by a hybridoma formed by fusing mouse lymphocytes and mouse myeloma cells. The monoclonal antibodies show specificity for a non-soluble, membrane associated, organ specific antigenic determinant limited in its distribution to human prostate epithelial cells and normal prostatic epithelial cells. The monoclonal antibodies, specifically, 7E11 monoclonal antibodies, can be used diagnostically and therapeutically.

14 Claims, 3 Drawing Sheets

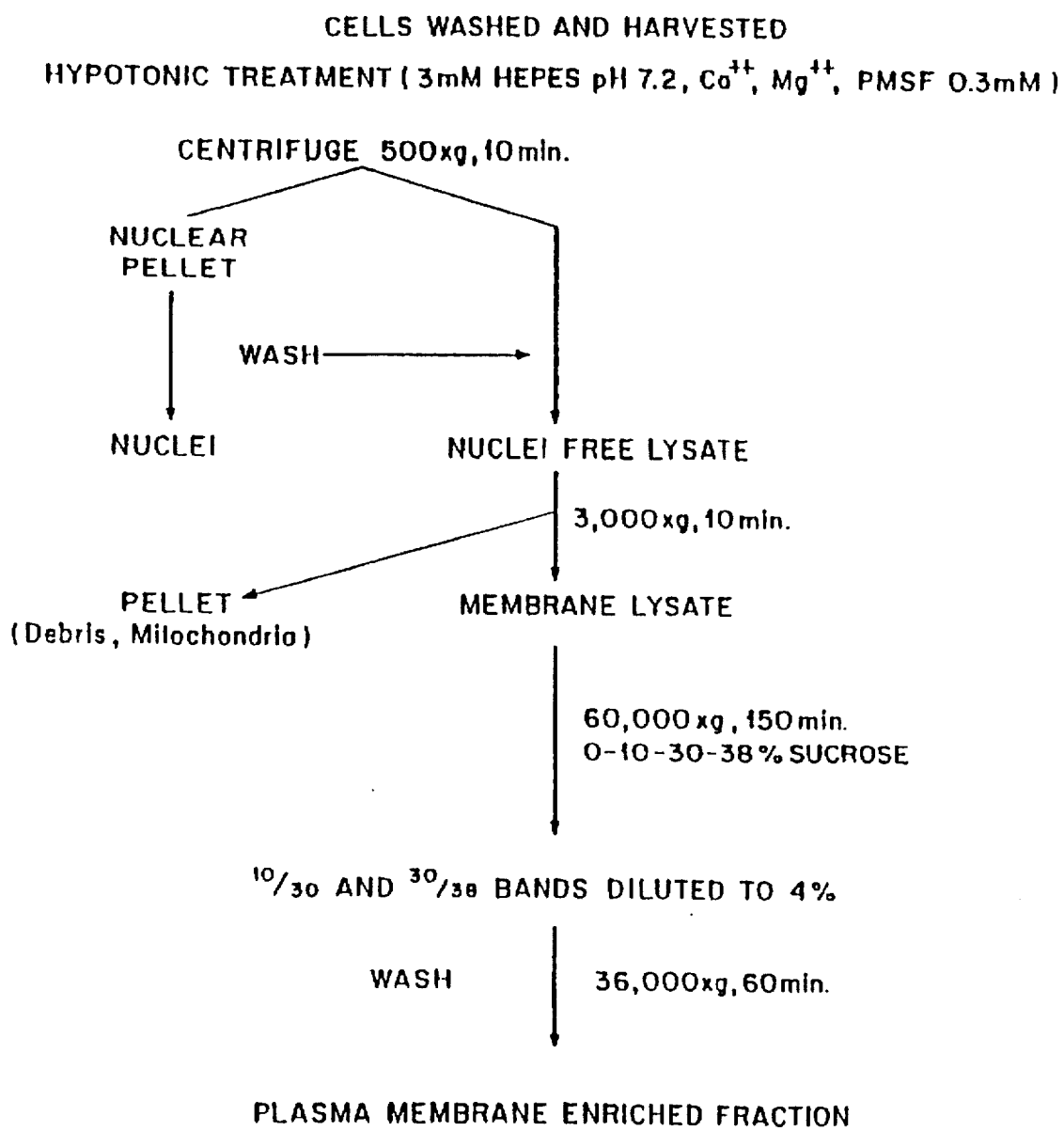

METHODS OF DETECTING PROSTATE CARCINOMA USING A MONOCLONAL ANTIBODY TO A NEW ANTIGENIC MARKER IN EPITHELIAL PROSTATIC CELLS ALONE OR WITH A MONOCLONAL ANTIBODY TO AN ANTIGEN OF LNCAP CELLS

This application is a continuation of application Ser. No. 08/307,544 filed Sep. 16, 1994, currently U.S. Pat. No. 5,578,484, which is a file wrapper continuation of application Ser. No. 07/822,500 filed Jan. 17, 1992, now abandoned, which in turn is a divisional of application Ser. No. 07/202,869 filed Jun. 3, 1988, now U.S. Pat. No. 5,162,504.

1. INTRODUCTION

This invention relates to the production of and applications for monoclonal antibodies specific for prostatic tumor antigens. More particularly, this invention relates to monoclonal antibodies against non-soluble, membrane associated, organ specific determinants expressed maximally on human normal and neoplastic prostatic epithelium. Monoclonal antibodies capable of reacting with membrane associated surface antigens are of value for the immuno-classification and detection of disease and represent novel agents for immunotherapy. The monoclonal antibodies of this invention possess distinctive characteristics and capabilities which make them suitable for in vitro clinical diagnostic and prognostic purposes. Moreover, they are of great potential importance for in vitro tumor localization and cancer therapy in humans.

The monoclonal antibodies exhibit a high level of binding to human prostatic cancer cells and normal prostatic epithelium and are potentially capable of experimental in vivo tumor localization. They bind to well-differentiated as well as to poorly-differentiated tumors.

The invention provides methods for production of the monoclonal antibodies by hybridoma techniques. Once cloned, cell lines can be maintained continuously to produce an unlimited homogeneous monoclonal antibody population that can be isolated and/or purified and used clinically for in vitro immunohistological, immuno-cytological or immuno-serological diagnosis, in vivo diagnosis by localization of tumors and metastases, and immunotherapy of human cancers, particularly those of the prostate.

2. BACKGROUND OF THE INVENTION

2.1. MONOCLONAL ANTIBODIES

Kohler and Milstein are generally credited with having devised the techniques that successfully resulted in the formation of the first monoclonal antibody-producing hybridomas [Kohler, G. and Milstein, C., Nature 256:495–497 (1975); Eur. J. Immunol. 6:511–519 (1976)]. By fusing antibody-forming cells (spleen lymphocytes) with myeloma cells (malignant cells of bone marrow primary tumors) they created a hybrid cell line, arising from a single fused cell hybrid (called a hybridoma or clone) which had inherited certain characteristics of both the lymphocytes and myeloma cell lines. Like the lymphocytes (taken from animals primed with sheep red blood cells as antigen), the hybridomas secreted a single type of immunoglobulin specific to the antigen; moreover, like the myeloma cells, the hybrid cells had the potential for indefinite cell division. The combination of these two features offered distinct advantages over conventional antisera. Whereas antisera derived from vaccinated animals are variable mixtures of polyclonal antibodies which never can be reproduced identically, monoclonal antibodies are highly specific immunoglobulins of a single type. The single type of immunoglobulin secreted by a hybridoma is specific to one and only one antigenic determinant, or epitope, on the antigen, a complex molecule having a multiplicity of antigenic determinants. For instance, if the antigen is a protein, an antigenic determinant may be one of the many peptide sequences [generally 6–7 amino acids in length (Atassi, M. Z., Molec. Cell. Biochem. 32:21–43 (1980))] within the entire protein molecule. Hence, monoclonal antibodies raised against a single antigen may be distinct from each other depending onthe determinant that induced their formation; but for any given clone, all of the antibodies it produces are identical. Furthermore, the hybridoma cell line can be reproduced indefinitely, is easily propagated in vitro or in vivo, and yields monoclonal antibodies in extremely high concentration.

2.2. APPLICATION OF MONOCLONAL ANTIBODIES TO CANCER

Monoclonal antibodies produced by hybridtoma technology are potentially powerful tools for cancer detection, diagnosis and therapy. [For a general discussion of the topic, see Hybridomas in Cancer Diagnosis and Treatment, Mitchell, M. S. and Oettgen, H. F., (eds.), Progress in Cancer Research and Therapy, Vol. 21, Raven Press, New York (1982)]. It has been reported that monoclonal antibodies have been raised against tumor cells [U.S. Pat. No. 4,196,265], carcinoembryonic antigen [U.S. Pat. No. 4,349,528], and thymocytes, prothymocytes, moriocytes and suppressor T cells [U.S. Pat. Nos. 4,364,933; 4,364,935; 4,364,934; 4,364,936; 4,364,937; and 4,364,932]. Recent reports have demonstrated the production of monoclonal antibodies with various degrees of specificity to several human malignancies, including prostatic carcinomas [Webb, K. et al., Canc. Immunol. Immunoth. 17:7–17 (1984), Carrol, A., Clin. Immun. and Immunopath. 33:268–281 (1984)], mammary tumor cells [Colcher, D. et al., Proc. Natl. Acad. Sci. U.S.A. 78:3199–3203 (1981)], lung cancers [Cuttitta, F., et al., Proc. Natl. Acad. Sci: U.S.A. 78:495–4595 91981)] malignant melanoma [Dippold, W. G. et al., Proc. Natl. Acad. Sci. U.S.A., 77:6114–6118 (1980)], colorectal carcinoma [Herlyn, M. et al., Proc. Natl. Acad. Sci. U.S.A. 76:1438–1442 (1979)], lymphoma [Nadler, L. M. et al., J. Immunol. 125:570–577 (1980)], and neuroectodermal tumors [Wikstrand, C. J. and Bigner, D. C., Cancer Res. 42:267–275 (1982].

Investigators have noted the potential immunotherapeutic value of monoclonal antibodies and some investigators have investigated therapeutic efficacy in both animal and human subjects [Oldham, R. K., J. Clin. Oncol., 1:582–590 (1983); Miller, R. A. et al., Blood, 62:988–995 (1983); Miller R. A. et al., New Engl. J. Med. 306:517–522 (1982); Ritz, J. and Schlossman, S., Blood, 59:1–11 (1982); and Kirch, M. E. and Ulrich, H. J. Immunol. 127:805–810 (1981)]. Although most studies have described the effects of cytotoxic drug-antibody conjugates, [Beverly, P. C. L., Nature, 297:358–9 (1982); Krolick, K. A. et al., Nature, 295:604–5 (1982); Krolick, K. A. et al., Proc. Natl. Acad. Sci. U.S.A., 77:5419–23 (1980); Arnon, R. and Sela, M., Immunol. Rev., 62:5–27 (1982); Raso, V. et al., Cancer Res., 42:457–64 (1982); and DeWeger, R. A. and Dullens, H. F. J., Immunol. Rev. 62:29–45 (1982)], experimental and clinical studies on passive immunotherapies have been attempted

[Sears, H. F. et al., Lancet, i:762–65 (1982); Rosenberg, S. A. and Terry, W. D., Cancer Res., 25:323–88 (1977); Herlyn, D. M. et al., Cancer Res., 40:717–21 (1980); Scheinberg, D. A. and Strand, M., Cancer Res. 42:44–9 (1982); Koprowski, H. et al., Proc. Natl. Acad. Sci. U.S.A., 75:3405–9 (1978); and Young, Jr., W. W. and Hakomori, S. I., Science, Science, 211:487–9 (1981)]. In the experimental setting, however, most studies have dealt with the concurrent administration of monoclonal antibody and tumor inoculum, or administration within several days of the implantation of tumor cells, resulting in a decreased tumor take or growth rate or xenografts. In this context, these data form a basis for the immunoprophylaxis of tumor development.

It is an object of the present invention to provide monoclonal antibodies having a broad range of utilities in both therapy and diagnostics of prostate cancer.

2.3. MONOCLONAL ANTIBODIES TO PROSTATE CELLS

Prostatic epithelium has limited distribution, does not carry out functions vital for the survival of a patient, and was shown to produce organ specific, albeit secretory, macromolecules. Cancer of the prostate is the second most frequent tumor of males in the United States. Unknown etiology, variable pathology, intricate relationship to endocrine factors, and anaplastic progression contribute to the complexity of this disease and limited effectiveness of available therapies. The progress toward establishing effective immunological methods for early detection and successful management of cancer of the prostate (hereinafter referred to as CaP) may depend on laboratory experimentation with most suitable models used as reagents for monoclonal antibody production. Similarly to other tumors, prostate cancer specific antigen has not been defined by monoclonal antibodies, although some CaP-associated epitopes were already identified, and will be reviewed below.

Several investigators have reported on the production of monoclonal antibodies against epitopes of various normal and malignant prostate cell components. [Carroll, A. et al., Clin. Immunol. Immunopath. 33:268–281 (1984); Webb, K. et al., Cancer Immunol. Immunoth. 17:7–17 (1984); Frankel, A. et al., Proc. Natl. Acad. Sci. U.S.A. 79:903–907 (1982); Frankel, A. et al., Cancer Res. 42:3714 (1982); Starling, J. et al., Cancer Res. 42:3084 (1982)].

Several monoclonal antibodies are available against two well characterized, purified to homogeneity, soluble glycoproteins produced and secreted by either normal or malignant human prostatic epithelium. Wang et: al. described a human prostate specific antigen (P.S.A.) that has a molecular weight of 34,000, and is present in human prostate, seminal plasma and CaP cells. Readily produced polyclonal and monoclonal antibodies to purified P.S.A. established this antigen as a serodiagnostic marker for CaP, a marker for human prostatic epithelial cells and an immunohistological marker for prostate neoplasms. Another strictly organ specific, well known marker protein of normal and neoplastic human prostatic cell is human prostatic acid phosphatase (PAP). PAP is a glycoprotein with molecular weight of 100,000 in which the aminoterminal sequence and carbohydrate composition has been established. Murine monoclonal antibodies identify 3 distinct antigenic determinants and several sensitive immunoassays to measure PAP were developed. Preliminary experiments suggest that monoclonal anti-PAP antibody has potential for antibody-directed radioimaging and monoclonal antibody targeted chemotherapy of prostate cancer. Both P.S.A. and PAP are secretory products of diagnostic value and can be detected, not only in cells, but also in plasma of patients with advanced CaP, nude mice bearing LNCaP tumors (derived from a metastic lesion of human prostatic carcinoma) and culture supernatants from malignant human prostatic cells expressing this marker. Such distribution of soluble antigens could impair the monoclonal antibodies in reaching their ultimate target—the malignant cell.

Another strategy in monoclonal antibody production against human prostatic cancer cells has been the utilization as immunogens of whole cells or fractionated cell preparations from established in vitro cultures of human malignant prostatic cells PC-3 [Kaighn, M. et al., Invest. Urol. 17:16 (1979)] and DU-145 [Stone, K. et al., Int. J. Cancer 21:274 (1978)]. Neither of these cells lines, however, maintain a full set of characteristic biological or biochemical markers characteristic of prostatic epithelium and malignant prostatic cells, e.g., production of secretory human prostatic acid phosphatase, organ specific prostate antigen, responsiveness to androgens or the presence of the Y chromosome. Such cells may not be optimally representative of the majority of prostatic tumors as seen by the clinician and pathologist. A variety of monoclonal antibodies selected for in depth studies by others have shown reactivity not only with cell surface or cytoplasmic antigens of prostate cancer cells, but also with cells for other malignancies and significantly, with non-prostatic normal human tissues.

Starling, J. et al. (Canc. Res. 42:3084–3089 (1982) reported that a short immunization schedule with DU-145 cells (days 0, 8 and 15) of BALB/c mice resulted in isolation of monoclonal antibody 83.21 which bound to surfaces of DU-145 cells. This monoclonal antibody was of the IgM class and did not bind to a variety of human tumors, normal tissues, several cell lines, nor to normal human prostatic epithelium. Membrane preparations from one metastatic CaP, PC-3 and DU-145 cells efficiently bound monoclonal antibody 83.21. The spectrum and degree of reactivities of this monoclonal antibody with different cells varied depending upon the antibody binding assays used such as immunofluorescence, complement dependent cytotoxicity or quantitative adsorption analysis. Epitopes detected by monoclonal antibody 83.21 were present on 58% primary CaP and, 17% CaP metastases. In addition significant cross-reactions with transitional cell carcinoma of the bladder, cytomegalovirus transformed human embryonic cell line as well as with proximal convoluted tubules of normal kidney were seen.

Wright, G. et al. [Canc. Res. 53:5509–5516 (1983)] immunizing mice with PC-3 cells obtained monoclonal antibody P 6.2. This antibody, also of the IgM class, reacted with 72% of paraffin embedded specimens of CaP, however lung cancer, breast cancer, pancreas cancer and human normal kidney also stained.

Ware, J. et al. [Canc. Res. 42:1215–1222 (1982)] produced monoclonal antibody alpha Pro-3 of the IgG2a subclass by immunizing mice with PC-3 cells. This antibody recognized an antigen (p54) concentrated in human primary prostatic carcinoma removed surgically. The antigen p54 is also present in variable amounts in extracts from benign prostatic hypertrophy (BPH), testicular tumors, kidney cancer, thyroid cancer, bladder cancer, ovarian cancer and in normal non-prostatic tissues. Cultured cells such as PC-3, human breast carcinoma (MDA-MB-231) and normal human fibroblasts (IMR90) all show surface binding of monoclonal antibody Pro-3. Binding of alpha Pro-3 to another CaP derived cell line, DU-145 is only minimal.

Another epitope of the p54 antigen is also recognized by monoclonal antibody alpha Pro-5.

Short term immunization with a mixture of three cell lines derived from human CaP led to the isolation of monoclonal antibody alpha Pro-13 by Webb, K. et al. [Canc. Immunol. Immunother. 17:7–17 (1984)]. In the solid phase binding assay this antibody reacted with 8 out of 10 extracts of CaP and benign prostate hypertrophy, but bladder cancer and kidney cancers were also positive, though to a smaller degree. Immunoperoxidase staining of frozen sections produced positive staining in epithelial cells in 4 out of 12 CaP and in 1 out of 6 BPH specimens. Cross-reactivity with non-prostatic tissue occurred with renal carcinoma, glands of the normal trachea, and vessel endothelium from testis and tonsils. Among cultured cells, PC-3, lung cancer, colon cancer and melanoma contained surface molecules recognized by alpha Pro-13. The antigen defined by monoclonal antibody alpha Pro-13 is a glycoprotein of 120,000 molecular weight (nonreduced) which is intrinsically stable on the cell surface with negligible release in cell culture supernatant or solubilized significantly only after CHAPS, but not Triton X-100 detergent treatment.

Several monoclonal antibodies reactive with surface components of normal and malignant human prostiatic epithelium were obtained by Frankel, A. [Proc. Natl. Acad. Sci. USA, 79:903–907 (1982)] who used membrane enriched fractions from benign prostatic hypertrophy for immunization. All of them exhibited significant cross-reactivity with either kidney, spleen, thymus, pancreas, bladder, lung thyroid or brain tissue.

Carroll, A. et al. [Clin. Immunol. Immunropath. 33:268–281 (1984)] raised monoclonal antibodies to PC-3 cells. One hybridoma—F77-129 (IgG3 subclass;) reacted with prostatic cancer cell lines (PC-3 and DU-145), 3 out of 4 breast cancer cell lines and one colon cancer line. Immunoperoxidase staining of human tissues confirmed binding to normal and malignant human prosatic and breast tissue. Radioiodinated F77-129 localized readily in tumors induced by injection of PC-3 cells into nude mice.

There is a need for monoclonal antibodies which are prostate specific and which will not cross reeict with other tissue types. The use of such antibodies can add significant information regarding functional classifications of individual prostate tumors to augment clinical classifications.

The pattern of staining for the monoclonal antibody of this invention is distinct from the reactivities of previously described monoclonal antibodies which recognize antigens expressed by prostate tumors. The monoclonal antibodies provided herein stain malignant prostate epithelial cells intensely, mostly on the periphery of cells with a small degree of heterogeneity. Normal prostate epithelial cells or benign prostatic hypertrophy cells showled either faint or only a moderate degree of staining. By comparison with the monoclonal antibodies described by Frankel (supra), the monoclonal antibodies of the invention do riot stain non-epithelial components of the prostate (fibers, muscle, stroma, vessels, etc.). Additionally no specific staining was observed in non-prostatic malignant tumors.

3. SUMMARY OF THE INVENTION

Prior to the present invention, applicant believes that a non-soluble, prostate cancer specific antigen has not been defined by monoclonal antibodies, although some cancer of the prostate-associated epitopes have been identified.

The present invention provides methods and compositions for producing novel monoclonal anti-prostate carcinoma antibodies with specific binding capabilities and encompasses the used said antibodies for cancer immuiaodiagnosis, prognosis and therapy in humans. Specifically, the invention provides novel hybridoma-derived monoclonal antibodies which demonstrate a narrow spectrum of organ-specific reactivity with non-soluble, membrane associated antigenic determinants (epitopes) present on normal neoplastic and malignant human prostatic epithelium. The monoclonal antibodies do not react specifically with non-prostatic tumors and other tissues. The monoclonal antibodies stain malignant prostatic cells intensely and non-malignant prostatic epithelium weakly.

In addition, to their use as in vitro immuno-histological reagents for cancer diagnosis, the present invention contemplates the use of the monoclonal antibodies for in vivo diagnosis. Because of their ability to target prostate carcinoma cells, the monoclonal antibodies can be used in tumor localization and in the monitoring of metastases.

The invention further contemplates the use of the monoclonal antibodies provided herein as a diagnostic and prognostic tool for detection of cancer of the prostate. The monoclonal antibodies provided herein can be used as in vitro immunoserological and immunocytological reagents on body fluids to detect the presence of the specific antigen and/or cells bearing antigen. The monoclonal antibodies thereby permit non-invasive diagnosis of prostate carcinomas and place the clinician in a better position to diagnose, monitor and treat prostate cancer.

The monoclonals of the present invention may also be useful in the detection of anti-idiotypic antibodies.

The present invention provides methodologies useful in research for the evaluation of parameters associated with the use of monoclonal antibodies against human tumors in passive human immunotherapy. The monoclonal antibodies can be used as probes to investigate the roles of antigen density, tumor growth rates, tumor size, cellular heterogeneity and other variables in the susceptibility of tumors to immunotherapy. The monoclonal antibodies may also induce a modification of the host anti-tumor immune response through the formation of anti-idiotypic antibodies to immune monoclonal antibodies.

The invention contemplates the use of the antibodies provided herein in covalent combination with radioactive, cytotoxic or chemotherapeutic molecules. For instance, the monoclonal antibodies can be conjugated to certain cytotoxic compounds, including, but not limited to, radioactive compounds, diphtheria toxin (chain A), ricin toxin (chain A), adriamycin, chlorambucil, daunorubicin, or pokeweed antiviral protein to enhance their tumoricidal effectiveness.

The present invention further contemplates the use of monoclonal antibodies in immunoadsorption procedures to effectively separate prostate cancer cells from marrow elements based upon antibody binding, and in procedures to eliminate malignant cells while sparing bone marrrow cells. Because such procedures require a tumor antigen, such as the one recognized by the monoclonal antibodies of this invention, which is not found on bone marrow stem cells or lymphoid cells, the monoclonal antibodies represent a reagent useful for eliminating disseminated prostate cancer cells from autologous bone marrow.

Because the monoclonal antibodies are produced by hybridoma techniques, the present invention provides theoretically immortal cell lines capable of consistently producing high titers of single specific antibodies against a distinct prostate carcinnoma antigen. This is a distinct advantage over the traditional technique of raising antibodies in immunized animals where the resulting sera contain multiple antibodies of different specificities that vary in both type and titer with each animal, and, in individual animals, with each immunization.

4. DESCRIPTION OF THE FIGURES

Figure 1:
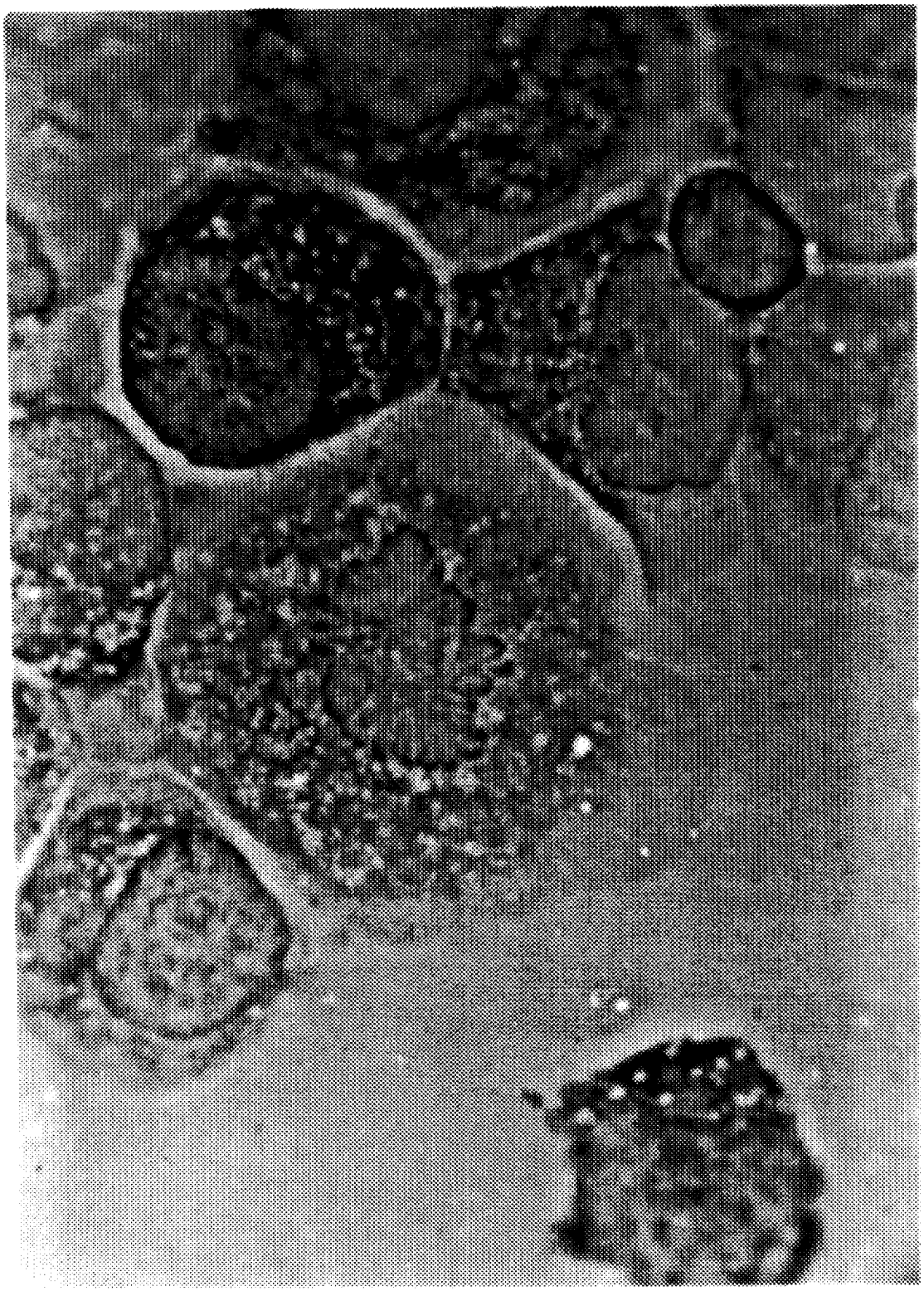
FIG. 1 is a photograph showing the indirect immonuperoxidase staining of LNCaP cells with monoclonal anitbody 7E11-C5.

FIG. 3 outlines the procedure used in preparing the LNCaP cell fraction used in immunization for monoclonal anitbody production.--

5. DESCRIPTION OF THE INVENTION

5.1. THE ANTIGEN

In the embodiment of the invention described in the Examples which follow, LNCaP prostate carcinoma cells and partially purified LNCaP plasma membranes were used as "antigen" or immunogen. As demonstrated by experiments described below, the epitope recognized by the antibody of this invention is present in several surgery and autopsy specimens from localized and metastatic prostate cancer, benign prostatic hypertrophy, normal prostates, and prostatic cultured cell lines. Hence, such cells expressing organ (or tissue) specific antigens also represent potential "antigen" or sources of antigen with which to immunize animals to obtain somatic cells for fusion.

5.2. SOMATIC CELLS

Somatic cells with the potential for producing antibody and, in particular B lymphocytes, are suitable for fusion with a B-cell myeloma line. Those antibody-producing cells that are in the dividing plasmablast stage fuse preferentially. Somatic cells may be derived from the lymph nodes, spleens and peripheral blood of primed animals and the lymphatic cells of choice depending to a large extent on their empirical usefulness in the particular fusion system. Once-primed or hyperimmunized animals can be used as a source of antibody-producing lymphocytes. Mouse lymphocytes give a3 higher percentage of stable fusions with the mouse myelomna lines described in section 5.3. However, the use of rat, rabbit, and frog cells is also possible.

Alternatively, human somatic cells capable of producing antibody, specifically B lymphocytes, are suitable for fusion with myeloma cell lines. While B lymphocytes from biopsied spleens or lymph nodes of individual may be used, the more easily accessible peripheral blood B lymphocytes are preferred. The lymphocytes may be derived from patients with diagnosed carcinomas.

5.3. MYELOMA CELLS

Specialized myeloma cell lines have been developed from lymphocyte tumors for use in hybridoma-producing fusion procedures [Kohler, G. and Milstein, C., Eur. J. Immunol. 6:511–519 (1976); M. Schulman et al., Nature 276: 269–270 (1978)]. The cell lines have been developed for at least three reasons. The first is to facilitate the selection of fused hybridomas among unfused and similarly indefinitely self-propogating myeloma cells. Usually, this is accomplished by using myelomas with enzyme deficiencies that render them incapable of growing in certain selective media that support the growth of hybridomas. The second reason arises from the inherent ability of lymphocyte tumor cells to produce their own antibodies. The purpose of using mono-clonal techniques is to obtain immortal fused hybrid cell lines that produce the desired single specific antibody genetically directed by the somatic cell component of the hybridoma. To eliminate the production of tumor cell antibodies by the hybridomas, myeloma cell lines incapable of producing light or heavy immunoglobulin chains or those deficient in antibody secretion mechanisms are used. A third reason for selection of these cell lines is for their suitability and efficiency for fusion.

Several myeloma cell lines may be used for the production of fused cell hybrids, including X63-Ag8, NSI-Ag4/1, MPC11-45.6TG1.7, C63-Ag8.653, Sp2/0-Ag14, FO, and S194/5XX0.BU.1, all derived from mice, 210.RCY3.Agl.2.3derived from rats and U-226AR, and GM1500GTGAL2, derived from rats and U-226AR, and GM1500GTGAL2, derived from humans , [G. J. Hammerling, U. Hammerling and J. F. Kearney (editors), Monoclonal Antibodies and T-cell Hybridomas IN: J. L. Turk (editor) Research Monographs in Immunology, Vol. 3, Elsevier/North Holland Biomedical Press, New York (1981) ].

5.4. FUSION

Methods for generating hybrids of antibody-producing spleen or lymph node cells and myeloma cells usually comprise mixing somatic cells with myeloma cells in a 2:1 proportion as in the example in Section 6.2. (though the proportion may vary from about 20:1 to about 1:1), respectively, in the presence of an agent or agents (chemical or electrical) that promote the fusion of cell membranes. It is often preferred that the same species of animal serve as the source of the somatic and myeloma cells used in the fusion procedure. Fusion methods have been described by Kohler and Milstein [Nature 256:495–497 (1975) and Eur. J. Immunol. 6:511–519 (1976)], and by Gefter et al. [Somatic Cell Genet. 3:231–236 1977)]. The fusion-promotion agent: used by those investigators were Sendai virus and polyethylene glycol (PEG), respectively. The fusion procedure of the example of the present invention is a modification of the method of Kohler and Milstein, supra.

5.5. ISOLATION OF CLONES AND ANTIBODY DETECTION

Fusion procedures usually produce viable hybrids at very low frequency, about $1 \times 10^{-6}$ to $1 \times 10^{-8}$. Because of the low frequency of obtaining viable hybrids, it is essential to have a means to select fused cell hybrids from the remaining unfused cells, particularly the unfused myeloma cells. A means of detecting the desired antibody-producing hybridomas among the other resulting fused cell hybrids is also necessary.

Generally, the fused cells are cultured in selective media, for instance HAT medium containing hypoxanthine, aminopterin and thymidine. HAT medium permits the proliferation of hybrid cells and prevents growth of unfused myeloma cells which normally would continue to divide indefinitely. Aminopterin blocks de novo purine and pyrimidine synthesis by inhibiting the production of tetrahydrofolate. The addition of thymidine bypasses the block in pyrimidine synthesis, while hypoxanthine is included in the media so that inhibited cells synthesize purine using the nucleotide salvage pathway. The myeloma cells employed are mutants lacking hypoxanthine phosphoribosyl transferase (HPRT) and thus cannot utilize the salvage pathway. In the surviving hybrid, the B lymphocyte supplies genetic information for production of this enzyme. Since B lymphocytes themselves have a limited life span in culture (approximately two weeks), the only cells which can proliferate in HAT media are hybrids formed from myeloma and spleen cells.

To facilitate screening of antibody secreted by the hybrids and to prevent individual hybrids from overgrowing others, the mixture of fused myeloma and B lymphocytes is diluted in HAT medium and cultured in multiple wells of microtiter plates. In two to three weeks, when hybrid clones become visible microscopically, the supernatant fluid of the individual wells containing hybrid clones is assayed for specific antibody. The assay must be sensitive, simple and rapid. Assay techniques include radioimmunoassays, enzyme immunoassays, cytotoxicity assays, plaque assays, dot immunobinding assays, and the like.

5.6. CELL PROPAGATION AND ANTIBODY PRODUCTION.

Once the desired fused cell hybrids have been selected and cloned into individual antibody-producing cell lines, each cell line may be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can be tapped to provide monoclonal antibodies in high concentration. Alternatively, the individual cell lines may be propogated in vitro in laboratory culture vessels; the culture medium, also containing high concentrations of a single specific monoclonal antibody, can be harvested by decantation, filtration or centrifugation.

5.7. IN VITRO DIAGNOSTIC USES FOR MONOCLONAL ANTIBODIES TO HUMAN PROSTATE CANCER

5.7.1. IMMUNOHISTOLOGICAL AND IMMUNOCYTOLOGICAL APPLICATIONS

The monoclonal antibodies of this invention can be used as probes in detecting discrete antigens in human tumors. The expression or lack of expression of these antigens can provide clinically exploitable information which is not apparent after standard histopathological evaluations. It may thus be possible to correlate the immuno-phenotypes of individual tumors with various aspects of tumor behavior and responsiveness to certain types of therapies, thus establishing important classifications of prognosis.

Monoclonal antibodies produced by the hybridoma is methodologies herein described can be used to detect potential prostate carcinoma cells in histological and cytological specimens and in particular, to distinguish malignant from non-malignant tumors based on staining patterns and intensities. For instance, using the immunoperoxidase staining technique described in section 6.7., it has been observed that the monoclonal antibodies of its invention stained neoplastic prostate cells, mostly on the periphery of cells, with a small degree of heterogeneity. Morphologically nonmalignant prostatic ductal, epithelium from benign prostatic hypertrophy and normal prostates generally exhibited a reduced degree of staining with cellular localization similar to prostatic cancer cells. Staining was completely absent from non-epithelial components of the prostate; no specific staining was observed in non-prostatic malignant tissues nor in normal human organs and tissues examined.

As an alternative to immunoperoxidase staining, immunofluorescent techniques can be used to examine human specimens with monoclonal antibodies to prostate carcinoma. In a typical protocol, slides containing cryostat sections of frozen, unfixed tissue biopsy samples or cytological smears are air dried formalin fixed and incubated with the monoclonal antibody preparation in a humidified chamber at room temperature.

The slides are then layered with a preparation of antibody directed against the monoclonal antibody, usually some type of anti-mouse immunoglobulin if the monoclonal antibodies used are derived from the fusion of a mouse spleen lymphocyte and a mouse myeloma cell line. This antimouse immunoglobulin is tagged with a compound that fluoresces at a particular wavelength for instance rhodamine or fluorescein isothiocyanate. The staining pattern and intensities within the sample are then determined by fluorescent light microscopy and optionally photographically recorded.

5.7.2. IMMUNOSEROLOGICAL APPLICATIONS

The use of the monoclonal antibodies described herein can be extended to the screening of human biological fluids for the presence of the specific antigenic determinant recognized. In vitro immunoserological evaluation of sera withdrawn from patients thereby permits non-invasive diagnosis of cancers. By way of illustration, human fluids, such as pleural fluids or lymph, can be taken from a patient and assayed for the specific epitope, either as released antigen or membrane-bound on cells in the sample fluid, using the anti-prostate carcinoma monoclonal antibodies in standard radioimmunoassays or enzyme-linked immunoassays known in the art or competitive binding enzyme-linked immunoassays.

5.8. IN VIVO DIAGNOSTIC AND THERAPEUTIC USES FOR MONOCLONAL ANTIBODIES TO HUMAN PROSTATE CANCER

5.8.1. TUMOR LOCALIZATION

The monoclonal antibodies of this invention are potentially useful for targeting prostate carcinoma cells in vivo. They can therefore be used in humans for tumor localization and for monitoring of metastases. For this application, it is preferable to use purified monoclonal antibodies. Purification of monoclonal antibodies for human administration by ammonium sulfate or sodium sulfate precipitation followed by dialysis against saline and filtration sterilization has been described by Miller et al. [IN: Hybridomas in Cancer Diagnosis and Therapy, (1982) supra, p. 134.] and by Dillman et al. [Id. p.155] which are hereby incorporated by reference. Alternatively, immuno-affinity chromatography techniques may be used to purify the monoclonal antibodies.

The purified monoclonal antibodies can be labeled with radioactive compounds, for instance, radioactive iodine, and administered to a patient intravenously. After localization of the antibodies at the tumor or metastatic site, they can be detected by emission tomographical and radionuclear scanning techniques thereby pinpointing the location of the cancer. Experimental radioimmunodetection with monoclonal antibodies by external scintigraphy has been reported by Solter et al. [Id., p.241] hereby incorporated by reference.

5.8.2. PASSIVE IMMUNOTHERAPY FOR TREATMENT OF HUMAN CANCER

Passive monoclonal serotherapy may be a potential use for the monoclonal antibodies of this invention. By way of illustration, purified anti-prostate carcinoma monoclonal antibody (see Section 5.8.1) is dissolved in an appropriate carrier e.g., saline, with or without human albumin, at an appropriate dosage and is administered to a patient The monoclonal antibodies are preferably administered intravenously, e.g., by continuous intravenous infusion over several hours, as in Miller et al., incorporated by reference, supra. Infusions can be administered over a period of weeks during which the anti-tumor effects are monitored.

In an alternate embodiment, the antibodies described herein are used to stimulate the production of corresponding anti-idiotypic antibodies. The experimental results observed in connection with this invention, i.e., the high percentage of binding of monoclonal antibody 7E11-C5 detected in a competitive inhibition ELISA, suggest that sera from prostatic cancer patients contain anti-idiotypic antibodies. In brief, anti-idiotypic antibodies, or antiidiotypes are antibodies directed against the antigen combining region or variable region (idiotype) of another antibody. In theory, based on Jerne's network model of idiotypic relationshps (Jerne, Ann. Immunol. 125:373, 1974; Jerne et al., EMBO 1:234, 1982), immunization with an antibody molecule expressing a paratope (antigen-combining site) for a given antigen should produce a group of anti-antibodies, some of which share with the antigen a complementary structure to the paratope. Immunization with a subpopulation of antiidiotypic antibodies should in turn produce a subpopulation of antiidiotypic antibodies which bind the initial antigen. Thus, the administration of the monoclonal antibodies of the present invention may result in a modification of the host's anti-tumor immune response, as the consequence of the formation of anti-idiotypic antibodies which may develop during therapy with the monoclonals.

5.8.3. TREATMENT OF HUMAN CANCER WITH MONOCLONAL ANTIBODY CONJUGATES

The monoclonal antibodies of this invention can be used in conjunction with a broad spectrum of pharmaceutical or cytotoxic agents such as: radioactive compounds (e.g., $In^{111}$, $I^{125}$, $I^{131}$); agents which bind DNA, for instance, alkylating agents or various antibiotics e.g., daunomycin, adriamycin, chlorambucil); antimetabolites such as methotrexate; agents which act on cell surfaces (e.g., venom phospholipases and microbial toxins); and protein synthesis inhibitors (e.g., diphteria toxin and toxic plant protein; enzymes that inhibit the action of eukaryotic ribosomes (egg. ricin, ricin A chain and pokeweed antiviral protein. [For reviews on the subject, see Bale et al., Cancer Research 40:2965–2972 (1980); Ghose and Blair, J., Natl. Cancer Inst. 61 (3):657–676 (1978); Gregoriadis, Nature 265: 407–411(1978); Gregoriadias, Pharmac. Ther. 10:103–108 (1980); Trouet et al., Recent Results Cancer Res. 75:229–235 (1989)]. Of particular importance are those agents capable of exerting toxic effects at the level of the cell surface, such as adriamycin [Tritton, T. R. and Yee, G., Science, 217:248–50 (1982)].

The methods used for binding the cytotoxic agents to the monoclonal antibody molecule can involve either non-covalent or covalent linkages. Since non-covalent bonds are more likely to be broken before the antibody complex reaches the target site, covalent linkages are, preferred. For instance, carbodiimide can be used to link carboxy groups of the pharmaceutical agent to amino groups of the antibody molecule. Bifunctional agents such as dialdehydes or imidoesters can be used to link the amino group of a drug to amino groups of the antibody molecule. The Schiff base reaction can be used to link drugs to antibody molecules. This method involves the periodate oxidation of a drug or cytotoxic agent that contains a glycol or hydroxy group, thus forming an aldehyde which is then reacted with the antibody molecule. Attachment occurs via formation of a Schiff base with amino groups of the antibody molecule. Additionally, drugs with reactive sulfhydryl groups have been coupled to antibody molecules.

Similarly, glycosidic enzymes such as neuraminidase or α-mannosidase can be conjugated to the monoclonal antibodies. Conjugated antibodies can be administered to patients to achieve enhanced tumoricidal effects through the cytotoxic action of the chemotherapeutic agents or the increased binding effect of the glycosidic enzymes.

6. EXAMPLES

6.1. CELL LINES AND TISSUES

The LNCaP cell line was established from a metastatic lesion of human prostatic carcinoma. The LNCaP cells grow readily in vitro (up to $8\times10^5$ cells/ $cm^2$; doubling time, 60 hours), form clones in semisolid media, and show an aneuploid (modal number, 76 to 91) human male karyotype with several marker chromosomes. The malignant properties of LNCaP cells are maintained. Athymic nude mice develop tumors at the injection site (volume-doubling time, 86 hours). Functional differentiation is preserved; both cultures and tumor produce a prostate acid phosphatase (PAP) and prostate specific antigen (P.S.A.). High-affinity specific androgen receptors are present in the cytosol and nuclear fractions of cells in culture and in tumors. Estrogen receptors are demonstrable in the cytosol. The model is hormonally responsive. In vitro, α-dihydro-testosterone modulates cell growth and stimulates acid phosphatase production. In vivo, the frequency of tumor development and the mean time of tumor appearance are significantly different for either sex. LNCaP cells, therefore, meet criteria of a versatile model for immunological studies of human prostatic cancer in the laboratory.

Seven malignant cell lines of human origin were obtained from J. Fogh of Memorial Sloan-Kettering Institute and included: DU-145 and PC-3 derived from prostatic cancer; MCF-7, derived from pleural effusion of scirrhous carcinoma of the breast [Soule, D. G. et al., J. Natl. Cancer Inst., 51:1409–1416 (1973)]; MeWo, malignant melanoma; RT-4, transitional cell carcinoma; HT-29, adenoma of the colon and A209, rhabdomyosarcoma. Four other cell lines (two malignant and two normal), isolated and established at Roswell Park Memorial Institute were also used. TT, thyroid medullary carcinoma, pancreatic cancer, BG-9 and MLD - both normal diploid neonatal foreskin fibroblast (see Horoszewicz et al., Infect. Immun. 19:720–726, 1978; Chen et al., Human Pancreatic Adenocarcinoma, Vol. 18: 24–32, 1982; Leong et al., Advances in Thyroid Neoplasia 1984:95–108, 1982). All of the above cell lines were routinely maintained in RPMI medium 1640 (Roswell Park Memorial Institute, Buffalo, New York) supplemented with 10% heat inactivated fetal bovine serum, 1 mM L-glutamine, and 50 µg/ml of penicillin and streptomycin (Gibco, Grand Island, N.Y.).

Fresh normal, benign and malignant prostate cancer tissues were obtained either from the Department of Surgery or the Department of Pathology at Roswell Park Memorial Institute. The tissues were quick frozen in M-1 embedding matrix (Lipshaw Corp., Detroit, Mich.) and stored at −80°C.

6.2. IMMUNIZATION AND CELL FUSION

Ten week old male Balb/c mice (West Seneca Laboratory, West Seneca, N.Y.) received intraperitoneal injections ($2 \times 10^7$ cells/0.2 ml) of washed (3 times in RPMI medium 1640, Roswell Park Memorial Institute, Buffalo, N.Y.) live LNCaP cells suspended in RPMI medium 1640, at monthly intervals for 3 months. Three days before fusion, the mice received an intraperitoneal challenge of $2 \times 10^7$ cells in RPMI medium 1640 and an intravenous injection of the plasma membrane isolated from $1 \times 10^8$ LNCaP cells. Cell fusion was carried out using a modification of the procedure developed by Kohler and Milstein [Nature (Lond.) 256:495–497 (1975)]. Mouse splenocytes ($1 \times 10^8$ cells) were fused in HyBRL-Prep 50% polyethylene glycol 1450, Bethesda Research Laboratories, Inc., Gaithersburg, Md.) with $5 \times 10^7$ mouse myeloma cells (P3×63Ag8.653). Fused cells were distributed to ten 96-well culture plates (Falcon, Oxnard, Calif.) and grown in hypoxanthine/aminopterin/thymidine (HAT) medium at 37° C. with 7.5% $CO_2$ in a humid atmosphere. Fourteen days later, supernatants were assayed for binding activity to plasma membrane isolate from LNCaP cells and MLD (normal human fibroblasts) using the Enzyme Linked Immunosorbent Assay (ELISA) with anti-mouse IgG β-galactosidase linked F(ab")$_2$ fragment from sheep (Amersham Corp., Amersham, England) or goat anti-mouse IgG horseradish peroxidase conjugate (Bio-Rad Laboratories, Richmond, Calif.) in a primary screen. Dried membrane isolate (400 ng/well) instead of whole LNCaP cells was used in the primary screening process because of poor attachment of the LNCaP cells to the plastic wells. To circumvent this problem, immuniofiltration on a disposable microfold system (V & P Scientific, San Diego, Calif.) using whole LNCaP cells was used as a confirmatory assay as described in Section 6.5. In addition, the dot-immunobinding assay on nitrocellulose membrane (Section 6.4) was used to screen the supernatants of hybridomas for reactivity against LNCaP cell cytosol ($100,000 \times g$ supernatants) and crude plasma membrane preparation. To determine the specificity spectrum of the cultures showing reactivity with the plasma membranes and/or whole LNCAP cells, the culture fluids were further tested by ELISA on a panel of an additional 9 viable, normal and neoplastic human cells lines as described in Section 6.5.

6.3. ISOLATION OF PLASMA MEMBRANE-ENRICHED) FRACTION

Plasma membrane-enriched fractions were obtained from LNCaP cells and normal human diploid fibroblast: strain MLD by modification of published methods [Kartner, N. et al., J.

Membrane Biol. 36:191–211 (1977)]. Briefly, MLJD cells in roller bottles or LNCaP cells in plastic culture flasks were gently rinsed 4 times with phosphate buffered saline (PBS). The cells were then rinsed once with hypotonic lysing buffer (3 mM Hepes [hydroxyethylpiperazine-ethanesulfonic acid], pH 7.0, 0.3 mM $MgCl_2$, 0.5 mM $CaCl_2$) and the buffer discarded.

Fresh lysing buffer (5–25 ml) was added to each bottle or flask and the cells allowed to swell for 30 minutes at room temperature. The swollen cells were removed from the surface and disrupted by manual shaking. The progress of disruption was monitored by phase microscopy of a sample droplet. Gentle trituration (8–10 times) with a 10 ml pipette was used to complete disruption of the LNCaP cells.

Vigorous shaking and pipetting were necessary to completely break-up the MLD cells. Phenyl-methylsulfonyl fluoride (PMSF, 0.5 mM) [Calbiochem, San Diego, Calif.) was added to minimize proteolysis. The disrupted cell suspensions were centrifuged at $100 \times g$ to remove nuclei and incompletely disrupted cell clumps. The nuclei pellet was washed once with the lysing buffer and after centrifugation the supernatant was combined with the first supernatant and centrifuged at $3,000 \times g$ for 10 minutes, at 4° C. The pellet consisting of mitochondria and debris was discarded and the supernatant designated as membrane lysate was layered over a discontinuous density gradient composed of 15 ml each of 10, 30 and 38% sucrose (w/v) and centrifuged at $60,000 \times g$ for 2½ hours in an SW 25.2 rotor (Beckman). Material banding at the interface between 10% and 30% sucrose layers was removed by aspiration, washed free of sucrose using lysing buffer and pelleted by centrifugation at $36,000 \times g$ for 60 minutes. Pellets were resuspended in PBS and aliquots taken for assay of protein and the enzyme phosphodiesterase-I (EC3.1.3.35) as a marker for plasma membranes. The 10/30 plasma membrane isolate was used in the screening assays for the hybridoma supernatants. All fractions were dispensed and stored as single-use aliquots at −90° C.

6.4. DOT-IMMUNOBINDING ASSAY

The dot-immunobinding assay was used to screen large numbers of supernatants of hybridomas producing monoclonal antibodies (Hawkes, et al. Anal Biochem. 119:142–147, 1982). The crude plasma membrane isolate, the 10/30 plasma membrane isolate and/or the cytosol fractions containing the cellular antigen were dotted (1–3 μl) on a washed nitrocellulose filter paper grid (Bio-Rad, Richmond, Calif.). The protein concentration of the "antigen" ranged from between 0.1 to 0.1 mg/ml. After thorough drying, the filter was washed in Tris Buffered Saline (TBS, 50 mM Tris-HCl, 200 mM NaCl, pH 7.4). Treatment of the filter paper with 3% (w/v) bovine serum albumin (Sigma, St. Louis, Mo.) in TBS for 15 minutes at room temperature resulted in the blockage of nonspecific antibody binding sites on the filter and on the walls of the plastic vessel used to carry out the reaction. The filter paper was then incubated with hybridoma supernatant or purified monoclonal antibody (2–20 μl/ml) for 60 minutes in several changes of TBS, the blocking step was repeated. A second antibody [Fab')$_2$ goat anti-mouse IgG] conjugated to horseradish peroxidase (Bio-Rad, Richmond, Calif.) (diluted 1:1000 in blocking solution) was added and incubation was carried out at 37° C. for 120 minutes. After washing with TBS the peroxidase activity was developed with 4-chloro-1-napthol (0.6 mg/ml in TBS, Merck Inc.) and hydrogen peroxide (0.01% v/v). A positive reaction appeared as a blue colored dot against the white filter background.

Immunoblotting of cytosol and membrane fractions indicated that the soluble cytosol fraction of LNCaP cells was not reactive, while sedimentable (approximately $105,000 \times g$) membrane associated fractions gave strongly positive spots with monoclonal antibody 7E11.

6.5. ENZYME LINKED IMMUNOSORBENT ASSAY (ELISA)

The enzyme linked immunosorbent assay (ELISA) was used for general enzyme immunoassay of antigen and screening for monoclonal antibody production. Target cells were seeded ($2$–$30 \times 10^4$ cells/ml) on microtiter plates (Falcon, Oxnard, Calif.) 4–7 days before assay. Nonspecific binding sites on the plates were blocked with 1% (w/v) swine gelatin in a special media, FL, formulated to keep the cells viable. The FL media consisted of Dulbecco's Modified Eagle Medium (Gibco, Grand Island, N.Y.) supplemented with 15 mM Hepes, 0.3% NaCl, 10 mM $NaN_3$, and swine gelatin (1% for blocking or 0.3% for washing) pH 7.2–7.4. Hybridoma culture fluids (50 μl per well) were added and incubation was carried out at 37° C. for 60 minutes. The plates were washed 4 times with FL media and F(ab')$_2$ goat anti-mouse IgG conjugated to horseradish peroxidase (1:1250 in 0.3% swine gelatin, 0.01 M PBS, Bio-Rad, Richmond, Calif.) was used in place of the β-galactoxidase conjugate. After washing, 100 μl of substrate (25 ml of 0.1 M citrate buffer pH 5.0, 10 μl of 30% H$_2$O$_2$ and 10 mg of α-phenylenediamine, Sigma, St. louis, Mo.) was added to each well. The plate was incubated for 30 minutes in the dark, and the reaction stopped with 50 μl of 2N H$_2$SO$_4$/well. The absorbance was determined at 490 nm using the Bio-Tek EIA reader.

Dried crude plasma membrane isolates from LNCaP cells or dried cells were used initially in the primary screening procedure of hybridoma culture fluids. Approximately 400 ng of membrane protein in 50 μl of buffer (S3 mM Hepes, 0.3 mM MgCl$_2$, 0.5 mM CaCl$_2$) was dried (35° C., overnight) in 96 well flat bottom microtirer plates (Falcon, Oxnard, Calif.). Nonspecific binding sites on the plates were blocked with 1% swine gelatin in PBS containing 0.1% NaN$_3$. With the exception of the wash buffer consisting of 0.01 M Hepes and 0.2 μM of PMSF in saline pH 7.6, all other reagents used were as described above for cell surface enzyme immunoassay.

LNCaP cells attach poorly to plastic wells and detach from the plastic surface during the ELISA procedure. To circumvent this problem immunofiltration on a disposable is microfold system (V & P Scientific, San Diego, Calif.) using whole LNCaP cells was employed as a confirmatory assay for the dried membrane assay. After nonspecific binding sites on the disposable microfold system was blocked with 5% human serum albumin (HSA) in PBS, 2.5×10$^4$ LNCaP cells in 100 μl of 5% HSA buffer was deposited on the filter discs with vacuum. After washing the filters with 0.3% gelatin in 0.01 M phosphate buffer, the plates were processed as described above. However, after incubation with substrate, the reaction mixture from each well (100 μ) was transferred to ½ area Costar plates (Costar, Cambridge, Mass.) before spectrophotometric determination on the EbIO-TEK EIA reader. Hybridomas were detected in approximately 500 culture wells. 206 hybridomas were successfully expanded and on primary ELISA screen, 126 reacted with partially purified LNCaP membranes, 92 reacted with intact LNCaP cells 76 reacted with normal human fibroblast-cells and membrane preparations. Further screening by ELISA and by immunoperoxidase staining on a panel of additional 11 viable, normal and neoplastic cell lines and by immunoblotting of cytosol and membranes fractions from LNCaP cells narrowed the field of 2 cloned hybridoma cell lines of particular interest, including MoAb 7E11 and 9H10.

Hybridoma cultures showing specificity restricted to the LNCaP cells and membranes were cloned by limiting dilution and subcloned in agarose [see e.g., Schreier, M. et al., Hybridoma Techniques, pp. 11–15, Cold Spring Harbor Laboratory, Cold Spring Harbor, N.Y. (1980)]. Stable cultures of antibody-producing hybridomas were expanded in complete media [RPMI 1640 media supplemented with 10% (w/v) heat-inactivated fetal bovine serum, 100 U/ml penicillin, 100 μg/ml streptomycin, and 10 μg/ml insulin (GIBCO) and cryopreserved. After cloning, two stable monoclonal hybridoma cell lines were obtained and designated as 7E11-C5 and 9H10-A4 respectively.

Exhausted culture fluids and mouse ascites fluids were the source of antibodies used for further studies. Ascites fluid from mice carrying the hybridoma cell line was used to obtain large quantities of monoclonal antibodies. Hybridoma cells for ascites fluid production were washed 2 times with RPMI 1640 medium and resuspended at a density of 1–5×10$^7$ cells/ml. Using a 20-gauge needle, 0.2 ml of the cell suspension was injected into the peritoneal cavity of female nude mice. Pristane was not routinely used to precondition the animals. Ascites fluid containing high titers of antibodies was regularly harvested 4–5 weeks after injection with the hybridoma cells.

6.6. ISOTYPING OF MONOCLONAL ANTIBODIES

Monoclonals 7E11-C5 and 9H10-A4 are of the IgG1 subclass, as determined by double diffusion gel precipitation with isotype specific antisera (Miles). Consistent with this finding were observations that Protein A conjugated with either fluoroscein or horseradish peroxidase (BIO-RAD) failed to react with smears of LNCaP cells following incubation with either monoclonal.

6.7. INDIRECT IMMUNOPEROXIDASE STAINING OF TUMOR SPECIMENS OF MONOCLONAL ANTIBODIES 7E11-C5

In a first set of experiments, cytospin smears of cultured cells, formalin-fixed cryostat (-25°C.) sections and sections of formalin fixed, paraffin embedded human tissues were used for immunoperoxidase staining as described previously [Heyderman, E. and Neville, A. M., J. Clin. Path., 30:138–140 (1976)]. Briefly, hydrated paraffin tissue section or formalin fixed cryostat sections and cytospin smears (2% paraformaldehyde, pH 7.5, 60 minutes, at room temperature) were treated with 10% pooled normal human serum in PBS; and washed for 15 minutes in PBS containing 0.5% Nonidet P-40. The sections were then incubated (60 min., 37° C.) with monoclonal antibody preparations (30 μl, 5–20 μg/ml) diluted in PBS containing 1% w/v BSA (Sigma). Following 4 washes in PBS, peroxidase conjugated goat antibodies against murine immunoglobulin (1:50 dilution in 1% bovine serum albumin (Bio-Rad) were applied for 60 minutes at 37° C. After thorough washing in PBS (4 changes), the peroxidase activity was revealed using diaminobenzidine (0.5 mg/ml): H$_2$O$_2$ (0.01%) substrate in 0.1 M Tris buffer pH 7.2. The sections were dehydrated in increasing concentrations of ethanol to xylene and then mounted in Permount (Fisher Scientific, Fairlawn, N.J.). In addition to the normal controls, control experiments which included PBS in place of the primary antibody, peroxidase-conjugated antibody alone and culture fluid from the myeloma cell line P3×63Ag8.653 were used. The intensity of the immunoreaction product was evaluated using a Zeiss microscope (40× objective; 10× ocular), and scored using a(−) to (+++) scale.

The reactivity of the two stable monoclonal antibodies with LNCaP cells, as well as 32 other human normal and malignant cell lines, is presented in Table I.

TABLE I

REACTIVITY OF MoAb 7E11-C5 AND MoAb 9H10-A4 WITH CULTURED HUMAN CELLS BY ELISA AND IMMUNOPEROXIDASE STAINING

| | | Reactivity with | |
|---|---|---|---|
| Human Cells in Culture | | MoAb 7E11-C5 | MoAb 9H10-A4 |
| LNCaP | Prostatic Ca | +++ | ++++ |
| DU145 | Prostatic Ca | − | − |
| PC-3 | Prostatic Ca | − | − |
| RT-4 | Bladder Ca | − | − |
| 5637 | Bladder Ca | − | − |
| MCF-7 | Breast Ca | − | − |
| MDA-MB-231 | Breast Ca | − | − |
| HT-29 | Colon Ca | − | − |
| SK | Colon Ca | − | − |
| COLO205 | Colon Ca | − | − |
| PAC | Pancreatic Ca | − | − |
| TT | Medullary Thyroid Ca | − | − |
| MeWo | Melanoma | − | − |
| SM | Melanoma | − | − |
| HeLa-S31 | Uterine Ca | − | − |
| HeLa-CCL2 | Uterine Ca | − | − |
| A209 | Rhabdomysarcoma | − | − |
| SW872 | Liposarcoma | − | − |
| HT1080 | Fibrosarcoma | − | − |
| 5959 | Osteogenic Sarcoma | − | − |
| SAOS-2 | Osteogenic Sarcoma | − | − |
| HBC | Bronchogenic Ca | − | − |
| A549 | Lung Adeno Ca | − | − |
| CHAGO | Large Cell Lung Ca | − | − |
| SKMES | Squamous Cell Lung Ca | − | − |
| PC-1 | Lung Ca | − | − |
| PC-9 | Lung Ca | − | − |
| PC-14 | Lung Ca | − | − |
| T-24 | Lung Ca | − | − |
| MLD | Normal Fibroblasts | − | − |
| BG-9 | Normal Fibroblasts | − | − |
| GM2504 | Normal Fibroblasts | − | − |
| FL | Human Amnion | − | − |

Figure 2:
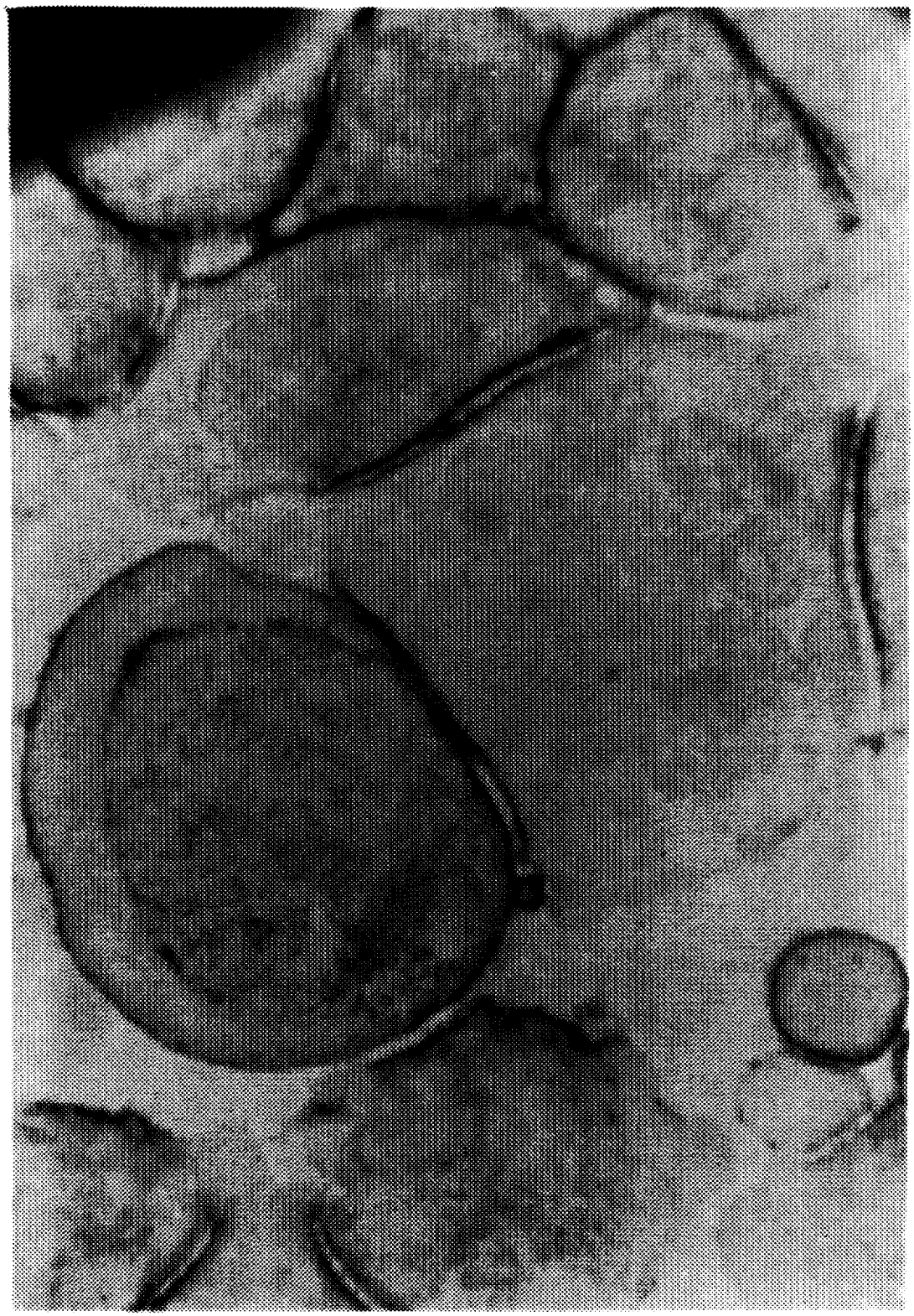
FIG. 2 is a photograph showing the indirect immunoperoxidase staining of LNCaP cells with monoclonal antibody 9H10-A4.

The indirect immunoperoxidase staining of formalin fixed LNCaP cells by supernatants from either of the hybridoma cultures was positive in dilutions ranging from 1:200 to 1:800 while ascitic fluids harvested from mice stained LNCaP smears at dilutions from 1:50,000 to 1:400,000. The localization of immunoperoxidase staining of LNCaP cells differed from MoAb 7E11-C5 and MoAb 9H10-A4. MoAb 7E11-C5 staining was apparent over the cytoplasmic region with intensity slightly increasing toward the cell periphery (FIG. 2). MoAb 9H10-A4 produced continuous, narrow band of strong staining associated with the cell periphery (FIG. 3). The staining pattern of LNCaP cells from culture, as well as cells taken directly from nude mouse tumors was constant for each MoAb.

Antigen reactive with MoAb 7E11-C5 was best preserved by neutral formalin or cold acetone fixation. Methanol, ethanol, propanol and chloroform reduced reactivity: ethyl ether, Nonidet (0.1%) and Triton X-100 were without effect. Drying and storage at −80° for more than 3 days;, regardless of fixation, as well as treatment with periodate or Bouin's fluid, destroyed the 7E11-C5 antigen, suggesting its sensitivity to oxidation. Specimens embedded in paraffin after formalin fixation retained only small fraction of the original reactivity. Antigen detected by MoAb 9H10-A4 appears to be more stable and was fully reactive after exposure to all tested fixatives, as well as after prolonged storage.

Viable LNCaP cells when stained by the indirect immunofluorescence method showed bright peripheral rings after exposure to MoAb 9H10-A4. No staining of viable cells, however, was seen with MoAb 7E11-C5.

None of the 32 other cell lines (normal or malignant) showed any reactivity with either ELISA or indirect immunoperoxidase staining, regardless of fixation.

In an expanded analysis of the distribution of the epitope recognized by these two antibodies, indirect immunoperoxidase staining of frozen sections after fixation in neutral formaldehyde was performed. Fresh frozen sections of human normal and neoplastic tissues obtained from biopsy, surgery and autopsy were fixed in 2% neutral formaldehyde. Results from observations made on 175 specimens are shown in. Table 2.

TABLE 2

ANTIGEN IN FROZEN SECTIONS FROM 175 SPECIMENS DETECTED BY INDIRECT IMMUNOPEROXIDASE STAINING WITH MoAbs 7E11-C5 AND 9H10-A4

| | Positive/Total Tested | |
|---|---|---|
| | MoAb 7E11-C5 Reactive | MoAb 9H10-A4 Reactive |
| Human Prostatic Epithelium | | |
| CaP foci in prostate | 9/9 | 0/9 |
| CaP metastases in lymph nodes | 2/2 | 0/2 |
| Benign prostatic hypertrophy | 5/7 | 0/7 |
| Normal prostates | 9/9 | 0/9 |
| Human Tumors (Non-Prostatic) | | |
| Breast Ca | 0/8 | 0/8 |
| Renal | 0/3 | 0/3 |
| Bladder Ca | 0/2 | 0/2 |
| Adrenal Ca | 0/2 | 0/2 |
| Colon Ca | 0/2 | 0/2 |
| Sarcoma | 0/2 | 0/2 |
| Squamous Cell Ca | 0/3 | 0/3 |
| Melanoma | 0/1 | 0/1 |
| Neuroblastoma | 0/1 | 0/1 |
| Uterine Ca | 0/1 | 0/1 |
| Pancreatic Ca | 0/1 | 0/1 |
| Normal Human Organs | | |
| Urinary Bladder | 0/5 | 0/5 |
| Ureter | 0/5 | 0/5 |
| Seminal Vesicles | 0/3 | 0/3 |
| Testis | 0/4 | 0/4 |
| Kidney | 2/14 | 0/14 |
| Ovary | 0/3 | 0/3 |
| Uterus | 0/3 | 0/3 |
| Breast | 0/3 | 0/3 |
| Bronchus | 0/4 | 0/4 |
| Lung | 0/5 | 0/5 |
| Liver | 0/7 | 0/7 |
| Spleen | 0/8 | 0/8 |
| Pancreas | 0/5 | 0/5 |
| Tongue | 0/2 | 0/2 |
| Esophagus | 0/1 | 0/1 |
| Stomach | 0/3 | 0/3 |
| Colon | 0/8 | 0/8 |
| Thyroid | 0/5 | 0/5 |
| Parathyroid | 0/1 | 0/1 |
| Adrenals | 0/4 | 0/4 |
| Lymph Node | 0/5 | 0/5 |
| Skeletal Muscle | 0/5 | 0/5 |
| Heart | 0/5 | 0/5 |
| Aorta | 0/3 | 0/3 |
| Vena Cava | 0/3 | 0/3 |
| Brain | 0/1 | 0/1 |
| Skin | 0/4 | 0/4 |

MoAb 7E11-C5 stained both malignant and apparently normal prostatic ephithelial cells with remarkable selectivity. No reactivity was seen in stromal components such as fibers, vessels, muscles, etc. Positive cells stained stronger toward the cell periphery. The staining showed a small degree of heterogeneity among individual cells. A difference was noted in the intensity of staining between normal and neoplastic epithelium. The staining of CaP cells was strong in 9 out of 11 specimens and of moderate intensity in the remaining 2. Apparently normal and hypertrophic prostatic glands showed faint (in 12 out of 16 specimens) to moderate (2 out of 16) staining. Two specimens from benign prostatic hypertrophy (BPH), which were classified as negative, contained only very few rudimentary structures reminiscent of prostatic ducts. Overall, 25 out of 27 specimens from prostates and CaP reacted with MoAb 7E11-C5.

Despite strong staining of cytoplasmic membranes of LNCal cells, MoAb 9H10-A4 failed to react in frozen sections with either normal prostatic epithelium or with neoplastic cells;.

Neither MoAb 7E11-C5 nor MoAb 9H10-A4 stained fresh frozen sections from any of the 26 specimens representing 11 different histological types of human non-prostatic tumors.

Among 122 individual specimens from 28 different normal human organs and tissues, 120 did not show any staining with MoAb 7E11-C5. In 2 instances (out of 14) of normal kidneys, poorly defined, low intensity, diffuse and uneven brownish deposits were detected on the inner surfaces and in the lumen of some of the Henle's loops. Pre-incubation of fixed sections with 1% albumin or gelatin solutions reduced such "staining". Similar reactions in the human kidney by the immunloperoxidase staining with various murine monoclonal antibodies were noted by other authors, but the significance, if any, or the specificity of such "staining" is at present unclear. Again, MoAb 9H10-A4 did not react with any of the 122 specimens from normal organs.

6.8. COMPETITIVE BINDING ELISA

After incubation of MoAb 7E11-C5 at appropriate concentrations (20–100 ng/ml) with whole LNCaP cells, hypotonic cell lysates, LNCaP cell sonicates or partially purified cell membranes, the original activity of MoAb 7E11-C5 as measured by ELISA was significantly and reproducibly reduced. The inhibition was a function of antigen concentration and the length of incubation time (results not shown). These observations suggested that MoAb 7E11-C5 reactive antigen could also be detected, if present, in human sera using appropriately designed assay.

Initial experiments were focused on the assay specificity and methodology. For these studies, 3 sera from CaP patients inhibiting MoAb 7E11-C5 in competitive binding ELISA were used. Centrifugation (2 hrs; 100,000×g) failed to sediment their inhibitory activity which suggested that the "inhibitor" in serum is not associated with circulating whole CaP cells, membrane vesicles or cell fragments, but represents the MoAb 7E11-C5 reactive epitope in a soluble form. This observation was unexpected since high speed centrifugation of either disrupted LNCaP cells, or spent LNCaP cell culture media yields anti-MoAb 7E11-C5 directed reactivity only in sedimentable fractions, indicating that the MoAb 7E11specific epitope is associated with insoluble supramolecular aggregates. The level of competitive binding ELISA, inhibitory activity against MoAb 7E11-C5 in human sera remained constant after 10 cycles of repeated freezing and thawing, heating to 56° for 30 min., 6 months storage at −80°, as well as after overnight incubation at 37° regardless of addition of protease inhibitors.

ELISA inhibitory activity was not due to the presence in tested sera of a human antibody with specificity similar to MoAb 7E11-C5, which could competitively block available antigenic sites on the LNCaP detector cells, nor were enzymatic activities of serum affecting the antigenic sites of LNCaP cells. This was shown by preincubation (up to 72 hrs.), of wells containing LNCaP cells with either "inhibitory" serum, non-inhibitory serum or PBS. The serum was then removed and MoAb 7E11-C5 activity was tested by standard ELISA procedure. No reduction in reaction intensity was observed between control wells and wells pre-incubated with inhibitory sera.

In addition, either the presence in sera of anti-murine IgG capable of binding MoAb 7E11-C5 or the existence of an unusual proteolytic activity directed against monoclonal antibodies in general, was excluded by pre-incubation of inhibitory sera with murine MoAb 9H10-A4 and showing that immunologic reactivity with LNCaP cells and membranes was unaffected.

Next, the possibility was investigated that "inhibitors" in positive CaP sera were unspecific and interacted only with the Fc portion of MoAb 7E11. To this end, the inhibition of immunoreactivity of 7E11F(ab')$_2$ antibody fragments by CaP sera was tested. The F(ab')$_2$ antibody fragments were as susceptible to inhibition by positive human sera from CaP as were the complete MoAb 7E11-C5.

Taken together, the above experiments indicate that observed ELISA inhibition results from specific immunological reaction between MoAb 7E11and corresponding antigen present in serum from some CaP patients.

The assay methodology for testing human sera from normal blood donors, non-prostatic malignancies and patients with prostatic cancer for specific binding of MoAb 7E11-C5 in limiting concentrations was established as follows:

Aliquots (125 µl) of serum were incubated (3 hrs., room temp.) with:

a) 125 µl of diluent (PBS with 0.3% bovine serum albumin, pH 7.2, sodium azide 0.05%)

b) 125 µl of MoAb 7E11(60 ng/ml in diluent)

c) 125 µl of MoAb 9H10 (6 ng/ml in diluent).

As references of total MoAb activity in the absence of serum, MoAb 7E11-C5 (30 ng/ml) and MoAb 9H10-A4 (3 ng/ml) in diluent only were used. In addition, each microtiter plate contained a set (12 wells) of external controls consisting of normal female serum preincubated separately with each MoAb and diluent.

The reaction mixtures were then incubated in a single 96 well microtiter plate (Falcon) overnight (18 hrs, 4° C.; quadruplicate wells, 50 µl/well) with air dried LNCaP cells (4×10$^4$ cells/well, 2.0% formaldehyde fixed for 30 min) to determine reactivity by ELISA. The results of the ELISA test (O.D. read at 490 nm) are expressed as the Specific Reactivity with MoAb 7E11-C5 factor (SR7E11factor). The SR7E11factor is calculated according to the formula:

$$SR_{7E11} = \frac{O.D.\ (7E11 + \text{diluent})}{O.D.\ (7E11 + \text{serum})} \cdot \frac{O.D.\ (9H10 + \text{serum})}{O.D.\ (9H10 + \text{diluent})}$$

The inclusion of MoAb 9H10 in the test allows to compensate for potential differences in kinetics of binding of MoAb to target LNCaP cells in high (50%) serum concentration, as well as for unexpected presence in individual sera of interfering macromolecules (anti-murine IgG,. enzymes, etc.). The MoAb 9H10-A4 strongly binds to LNCaP plasma membranes, but is unrelated in specificity to MoAb) 7E11-C5 and does not react with other human cell lines, or frozen sections of normal human organs or malignant tumors. Neither normal nor CaP sera inhibit specifically MoAb 9H10-A4.

To examine the kinetics of SR7E11 factor changes, normal control and positive CaP sera were preincubated with MoAbs 7E11-C5 and 9H10-A4 for periods ranging from 3 hrs. up to 10 days. The antigen-antibody reaction was thus allowed to proceed to or near completion at limiting antibody concentrations. Table 3 shows that the SR7E11 factor of positive CaP sera significantly increases during prolonged serum-MoAb incubation, while $SR_{7E11}$ of control sera remains low or even decreases. This further supports the notion that $SR_{7E11}$ factor reflects the amount of antigen in serum binding MoAb 7E11. Another explanation is also plausible: sera from prostatic cancer patients could contain antiidiotypic antibodies (anti-Id) of the Ab-2 variety. Such antibodies could carry specificity and reactivity similar to the epitope associated with insoluble membranes of LNCaP cells, i.e., the epitope against which the murine monoclonal 7E11-C5 is directed. Therefore, the anti-Id could bind to 7E11-C5 and be the cause of positive results in the competitive inhibition ELISA in CaP serum.

TABLE 3

CHANGES IN $SR_{7E11}$ FACTOR AS A FUNCTION OF PRE-INCUBATION TIME OF MoAbs WITH HUMAN SERA

| Serum Source | Time of Pre-incubation with MoAbs | | | |
|---|---|---|---|---|
| | 3 Hrs. | 3 Days | 5 Days | 10 Days |
| Normal Female | 1.28 | 1.33 | 0.98 | 1.19 |
| Normal Male | 1.14 | 1.32 | 1.21 | 1.09 |
| Pool of Young Males | 1.19 | 1.43 | 1.28 | 0.99 |
| Prostatic Ca N° 1 | 2.07 | 4.11 | 6.83 | 7.34 |
| Prostatic Ca N° 2 | 3.07 | 10.64 | 14.30 | 15.95 |

To establish the average numerical value of $SR_{7E11}$ factor for normal, healthy individuals, 30 sera from RPMI Blood Bank donors were tested. The mean $SR_{7E11}$ of this group was $1.13 \pm 0.23$ ($\bar{x} \pm S.D.$). No significant differences between the mean values of the $SR_{7E11}$ factor for groups of males and females were found. For the threshhold defining positive results (at the p<0.01 level), $\bar{x} + 3$ S.D. was calculated to be 1.82. The value above 1.82 for $SR_{7E11}$ was used for the classification of Specific Reactivity as positive.

Subsequently, additional 116 sera were tested: 43 from CaP patients, 7 from individuals with benign prostatic hypertrophy and 66 sera from non-prostatic malignancies. Tables, 4, 5 and 6 show the results. A strong statistical correlation emerged between the assay positive outcome and diagnosis of prostatic cancer (Table 4). In addition, as shown in Table 5, the patients with positive $SR_{7E11}$ were more likely to be in progression than those who were negative. Similarly, a higher percentage of positive tests were among patients with widely disseminated disease vs. less advanced clinical stages. Among 66 sera from individuals with tumors of non-prostatic origin, only 3 (4.6%) tested positive (Table 6). Two of the positive sera were from females with disseminated uterine and renal carcinomas respectively. The third positive serum was obtained from young male with testicular embryonal carcinoma.

TABLE 4

SUMMARY TABLE OF MoAb 7E11-C5 COMPETITIVE BINDING ELISA IN HUMAN SERA

| Serum Source | Number Tested | $SR_{7E11}$ Positive |
|---|---|---|
| Prostatic Cancer (CaP) | 43 | 20 (46.5%) |
| Benign Prostatic Hypertrophy (BPH) | 7 | 0 |

TABLE 4-continued

SUMMARY TABLE OF MoAb 7E11-C5 COMPETITIVE BINDING ELISA IN HUMAN SERA

| Serum Source | Number Tested | $SR_{7E11}$ Positive |
|---|---|---|
| Non-Prostatic Malignancies | 66 | 3 (4.6%) |
| Normal Blood Donors | 30 | 0 |
| Total | 146 | 23 |

Two tail Fisher Exact Probability Test indicates that there is a significantly higher $SR_{7E11}$ positive rate (p<0.0001) in a population of 43 CaP patients as opposed to a group of 103 non-CaP controls (normal, BPH and other malignancies). The assays were blinded.

TABLE 5

MoAb 7E11-C5 COMPETITIVE BINDING ELISA IN PROSTATIC CANCER

| Clinical Evaluation | Number Tested | $SR_{7E11}$ Positive |
|---|---|---|
| No Apparent Disease | 7 | 0 |
| Remission/Stable | 13 | 6 (46%) |
| Progression | 23 | 14 (61%) |
| Total | 43 | 20 |
| CaP Stage | | |
| B I | 2 | 0 |
| B II | 5 | 1 (29%) |
| C I | 3 | 2 |
| D I | 4 | 1 |
| D II | 29 | 16 (55%) |
| Total | 43 | 20 |

Logistic regression relating the probablity that the patient was in caP progression to the $SR_{7E11}$ indicates a significant (at p<0.005) relationship. Patients with positive $SR_{7E11}$ are more likely to be in progressiion, than those who are negative. The assays were blinded.

TABLE 6

MoAb 7E11-C5 COMPETITIVE BINDING ELISA IN HUMAN SERA FROM NON-PROSTATIC MALIGNANCIES

| Diagnosis | $SR_{7E11}$ Positive/Total Tested |
|---|---|
| Testicular Tumors (Seminoma, Embryonal Ca, Teratoma) | 1/16 |
| Transitional Cell Ca (Bladder) | 0/7 |
| Renal Cell Ca | 1/4* |
| Breast Ca | 0/3 |
| Ovarian Adeno Ca | 0/3 |
| Uterine Adeno Ca | 1/2* |
| Gastric Ca | 0/3 |
| Hepatoma | 0/2 |
| Pancreatic Adeno Ca | 0/3 |
| Colon and Rectum Adeno Ca | 0/3 |
| Lung Ca | 0/3 |
| Sarcoma | 0/4 |
| Astrocytoma, Chordoma | 0/2 |
| Squamous Cell Ca | 0/3 |
| Basal Cell Ca | 0/2 |
| Histiocytoma | 0/1 |
| Mesothelioma | 0/1 |
| Lymphoma, Leukemia | 0/4 |
| Total | 3/66 (4.6%) |

MoAb 7E11-C5 and MoAb 9H10-A4 were of the IgG1 subclass and as such, either alone or with complement, lacked detectable biological activities against LNCaP cells in vitro or in nude mice. Both MoAbs reacted in ELISA and by immunoblotting with sedimentable, cytoplasmic membrane rich fractions of LNCaP cells, but not with soluble cytosol or secretory glycoproteins such as PSA or PAP. The antigen with which 7E11-C5 reacts, in cultured LNCaP cells, is strictly associated with non-soluble, sedimentable material. In contrast, many CaP patients' serum contains such epitopes in soluble form.

MoAb 9H10-A4 had specificity restricted to epitopes present on the surface of LNCaP cell plasma membrane as demonstrated by ELISA and immunospecific staining of a variety of viable or fixed cells and frozen sections. No binding of MoAb 9H10-A4 was detected to any other than LNCaP human prostatic and non-prostatic normal or malignant cells in studies involving 32 cell lines, 27 prostates and 148 other fresh-frozen specimens of human organs, normal tissues and tumors. This suggests that MoAb 9H10-A4 defined antigen could be unique for an individual prostatic tumor or perhaps even a single metastasis from which the LNCaP cells were isolated. However, since our study involved only 18 specimens from CaP, all of which were negative, an additional possibility remains that MoAb 9H10-A4 could be detecting epitopes which are associated with a rapidly progressing in younger males rare form of CaP from which LNCaP cells were originally isolated. Before these speculations are experimentally tested, MoAb 9H10-A4 remains as a useful reagent to positively identify LNCaP cells and distinguish them from other cultured cells. In addition, this MoAb serves as a reliable control in competitive binding ELISA with MoAb 7E11-C5 for detection of circulating antigens associated with CaP.

MoAb 7E11-C5 reacted with epithelial cells in frozen sections from prostatic carcinoma, benign prostatic hypertrophy and to a lesser degree with normal prostatic glands. Among 33 grown in vitro normal and neoplastic cell lines, only LNCaP cells bound MoAb 7E11-C5 in ELISA and in indirect immunospecific staining of dried and fixed smears. It is of interest that CaP derived DU-145 and PC-3 cells did not, exhibit any reactivity with MoAb 7E11-C5. This finding parallels the absence or diminution of phenotypic expression in PC-3 and DU-145 of other marker molecules (PAP, PSA, androgen receptors) which are characteristic of human epithelial prostatic cells, and are abundantly preserved in LNCaP cultures (Kaighn, et al., in Models for Prostatic Cancer, pp. 85–109, Alan R. Liss, Inc., N.Y., 1980; Kaighn et al., Invest. Urol. 17:16–23, 1979; Papsidero et al., Cancer Res. 40:3032–3035, 1980; Stone et al. Int. J. Cancer 21:2374–281, 1978). Strong reactivity of MoAb 7E11-C5 with LNCaP membrane preparations and fixed cells contrasted sharply with the lack of staining by the indirect immunofluorescence method of viable, unfixed LNCaP cell suspensions. This observation suggests that epitopes specific for MoAb 7E11-C5 are either absent or not available for binding on the outer surface of living LNCaP cells. It remains to be determined whether such restriction applies to normal and malignant viable cells from human prostates. The results of such experiments could help to project the practical potential of appropriate MoAb 7E11-C5 conjugates as either imaging or therapeutic agents for CaP.

The evidence for selective specificity of MoAb 7E11-C5 for human prostatic epithelium was reinforced by consistently negative results of immunospecific staining of numerous fresh frozen sections from a wide range of human non-prostatic normal or malignant tissues. Noted on a couple of occasions, poorly defined staining of kidney tubules require additional observations to ascertain its reproducibility and specificity on a larger size sample of fresh biopsy specimen.

Cell lines 7E11-C5 and 9H10-A4 as described herein have been deposited with the American Type Culture collection, International Depository Authority, 12301 Parklawn Drive, Rockville, Md. 20852,on Jun. 29, 1990 and Aug. 5, 1993, respectively, and have been assigned accession number ATTC No. HB10494 and HB 11430 , respectively. The invention described and claimed herein is not to be limited in scope by the cell line deposited, since the deposited embodiment is intended as a single illustration of one aspect of the invention and any equivalent cell lines which produce a functionally equivalent monoclonal antibody are within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for detecting prostate carcinoma which comprises: contacting a monoclonal antibody having the epitope binding specificity of the monoclonal antibody produced by the hybridoma cell line 7E11-C5 assigned ATCC accession No. HB 10494, which antibody binds specifically to an epitope present on a membrane asociated antigen of human prostatic cancer epithelium and normal epithelium but not to non-prostatic antigens in other tissues, with a human tissue sample, and detecting an interaction of said antibody with prostate carcinoma cells bearing the prostate epithelium-specific antigen in the human tissue sample.

2. The method according to claim 1 wherein the human tissue is prostate tissue.

3. The method of claim 1, wherein the interaction is detected by immunohistological staining.

4. The method according to claim 1, wherein the monoclonal antibody is monoclonal antibody 7E11-C5 produced by hybridoma cell line designated ATCC accession No. HB 10494.

5. A histological method of detecting prostate carcinoma comprising: incubating a sample of a body tissue with a primary monoclonal antibody having the epitope binding specificity of the antibody produced by the cell line 7E11-C5 assigned ATCC accession No. HB 10494, which antibody binds specifically to an epitope present on a membrane associated antigen of human prostatic cancer epithelium and normal prostatic epithelium but not to non-prostatic antigens in other tissues; detecting bound primary antibody using a secondary antibody with specificity for said primary antibody, said secondary antibody being conjugated to a label; and visualizing the localization of said label bound in said sample.

6. The method according to claim 5, wherein said body tissue is suspected prostate carcinoma or suspected metastatic prostatic carcinoma.

7. The method according to claim 5, wherein said body tissue is prostate tissue.

8. An immunosorbent method of detecting prostate carcinoma in a human patient, comprising measuring the level of an antigen recognized by a monoclonal antibody produced by cell line 7E11-C5 assigned ATCC accession No. HB 10494 in a human tissue sample by a radioimmunoassay or enzyme immunoassay method.

9. An enzyme linked immunosorbent method for detecting prostate carcinoma in a human patient, comprising measuring the level of an antigen recognized by a monoclonal antibody produced by the hybridoma cell line 7E11-C5 assigned ATCC accession No. HB 10494 in a human tissue sample by:

(a) preincubating a sample of said tissue containing an unknown amount of said antigen with a monoclonal antibody having the epitope binding specificity of the monoclonal antibody produced by the cell line 7E11-C5 assigned accession ATCC No. HB 10494, which 7E11-C5 antibody binds specifically to an epitope present on a membrane associated antigen of human prostatic cancer epithelium and normal prostatic epithelium but not to non-prostatic antigens in other tissues;

(b) allowing sufficient time for the formation of monoclonal antibody-antigen complexes; and (c) testing the residual unbound monoclonal antibody activity in the mixture from step (b) in an ELISA assay comprising:
  (i) reacting the mixture with a solid phase coated with antigen recognized by said monoclonal antibody used in step (a);
  (ii) detecting monoclonal antibody bound using an enzyme-conjugated antibody with specificity for said monoclonal antibody;
  (iii) reacting bound enzyme-conjugated antibody with an appropriate substrate; and
  (iv) quantitating the percent inhibition of binding of said monoclonal antibody by said sample of tissue by comparison with a normal standard control sample.

10. The method for detecting prostate carcinoma in a human patient according to claim 9, in which the antigen used in step (c)(i) comprises: LNCaP cells, a lysate of LNCaP cells, an extract of LNCaP cells, and a plasma membrane enriched fraction of LNCaP cells.

11. The method of claim 9, wherein the monoclonal antibody is monoclonal antibody 7E11-C5 produced by hybridoma cell line designated ATCC accession No. HB 10494.

12. A non-invasive method for detecting prostate carcinoma, comprising assessing the level of antigen specific for prostate carcinoma in a sample of human body fluid by conducting a competitive binding enzyme-linked immune assay (ELISA), in which two separate aliquots of the biological fluid are incubated first with (a) diluent plus a first monoclonal antibody which binds specifically with prostatic cancer epithelial cells and normal prostate but does not bind to non-prostatic antigens in other tissues; or (b) diluent plus a second monoclonal antibody which binds to LNCaP cells but not to other human cell lines nor to normal or neoplastic human prostate cells; and then with immobilized LNCaP antigen; and expressing the results of the competitive binding ELISA assay as a specific reactivity factor (SR factor) calculated according to the formula:

$$SR \text{ factor} = \frac{O.D. \text{ [first monoclonal + diluent] antibody}}{O.D. \text{ [first monoclonal + body fluid] antibody}} - \frac{O.D. \text{ [second monoclonal + body fluid] antibody}}{O.D. \text{ [second monoclonal + diluent] antibody}}$$

where a positive SR factor, defined as about 3 standard deviations above the mean of that obtained using body fluid from a normal human, is indicative of prostate carcinoma, wherein the first monoclonal antibody is a monoclonal antibody having the epitope binding specificity of the monoclonal antibody 7E11-C5 produced by the hybridoma cell line assigned accession No. HB 10494 and the second monoclonal antibody is a monoclonal antibody having the epitope binding specificity of the monoclonal antibody 9H10-A4 produced by the hybridoma cell line assigned accession No. HB 11430.

13. The method according to claim 12, in which the first antibody is the monoclonal antibody 7E11-C5 produced by the hybridoma cell line assigned accession No. HB 10494 and the second monoclonal antibody is the monoclonal antibody 9H10-A4 produced by the hybridoma cell line assigned accession No. HB 11430.

14. The method according to claim 12, in which the human body fluid is serum.

* * * * *